United States Patent [19]

Datta et al.

[11] Patent Number: 4,808,387
[45] Date of Patent: Feb. 28, 1989

[54] STABILIZATION OF VANADIUM TETRACHLORIDE

[75] Inventors: Sudhin Datta, Scotch Plains, N.J.; Trazollah Ouhadi, Liege, Belgium

[73] Assignee: Exxon Chemical Patents Inc., Linden, N.J.

[21] Appl. No.: 50,945

[22] Filed: May 15, 1987

[51] Int. Cl.$^4$ .............................................. C01G 31/04
[52] U.S. Cl. .................................. 423/265; 502/224; 502/500
[58] Field of Search ............... 423/265, 492; 502/224, 502/500

[56] References Cited

U.S. PATENT DOCUMENTS

| | | | |
|---|---|---|---|
| 3,494,728 | 2/1970 | Letson et al. | 423/492 |
| 3,622,548 | 11/1971 | Emde et al. | 260/80 |
| 4,159,965 | 7/1979 | Sakurai et al. | 502/116 |
| 4,202,866 | 5/1980 | Feng et al. | 423/265 |
| 4,420,595 | 12/1983 | Evens | 526/141 |
| 4,435,552 | 3/1984 | Evens | 526/140 |
| 4,507,449 | 3/1985 | Martin | 526/122 |
| 4,514,514 | 4/1985 | Martin | 502/121 |

Primary Examiner—John Doll
Assistant Examiner—Jeffrey E. Russel
Attorney, Agent, or Firm—J. B. Murray, Jr.; W. G. Muller

[57] ABSTRACT

Vanadium tetrachloride is stabilized by the addition of minor but stabilizing amounts of an acyl halide, benzoyl chloride being especially preferred. The vanadium tetrachloride may be dissolved in an inert organic solvent; hydrocarbons such as hexane are preferred. The stabilized vanadium tetrachloride may be utilized subsequently in polymerization processes.

14 Claims, No Drawings

STABILIZATION OF VANADIUM TETRACHLORIDE

FIELD OF THE INVENTION

The present invention relates to a method for stabilizing solutions of vanadium tetrachloride. More particularly, the invention pertains to the stabilization of vanadium tetrachloride in hydrocarbon solutions, such vanadium tetrachloride solutions being suitable in the formulation of polymerization catalysts. The invention further encompasses the stabilized vanadium tetrachloride composition per se.

DESCRIPTION OF THE PRIOR ART

The instability of vanadium tetrachloride is well known. Thus, in U.S. Pat. No. 4,202,866 the problem is discussed and is said to exist regardless of the method employed for the preparation of vanadium tetrachloride. The disclosure in column 1, lines 11 to 56, and column 2, lines 24 to 54, of U.S. Pat. No. 4,202,866, pertaining to some of the established methods of preparing the vanadium tetrachloride, is incorporated herein by reference.

The stabilization of vanadium tetrachloride is also discussed in a somewhat earlier patent, U.S. Pat. No. 3,494,728, that is primarily concerned with an improved method of manufacturing vanadium tetrachloride. In column 2, lines 27 to 38, it is stated that improved yields are obtained if the inventive process is carried out in the presence of elemental chlorine and a fully chlorinated hydrocarbon, preferably a fully chlorinated diolefin. The patentees postulate that "the chlorinated hydrocarbon serves to maintain the chlorine in solution to some extent and thus tends to stabilize the tetrachloride."

Even at ambient temperatures the tendency of vanadium tetrachloride to decompose, even at ambient temperatures, is a serious commercial concern. As recognized by the prior art, the product of this decomposition is vanadium trichloride, which precipitates from the liquid vanadium tetrachloride or an organic solution thereof as a solid residue. Such residues adversely affect product quality and the pumpability of the vanadium tetrachloride solution. Moreover, this decomposition problem has severely hindered the commercial exploitation of vanadium tetrachloride, particularly as a polymerization catalyst component for the production of ethylenepropylene copolymers in spite of demonstrated higher catalyst activity, increased catalyst life, and superior product microstructure in the polymer chain.

Since the use of highly or fully chlorinated hydrocarbons have the potential of producing undesirably chlorinated by-products that could end up in the polymer products and must be removed therefrom, it would be very advantageous to have an effective vanadium tetrachloride stabilizer with limited halogenation. It is also important for the stabilizer not to deleteriously affect the polymerization catalyst composition or process when the vanadium tetrachloride is employed as a catalyst component.

SUMMARY OF THE INVENTION

In accordance with the present invention it has now been found that vanadium tetrachloride can be effectively stabilized with acyl monohalides, preferably aromatic monoacyl halides. For most purposes, the especially preferred aromatic monoacyl halide is benzoyl chloride. In addition to the method of stabilizing the vanadium chloride, in undiluted form as well as in an inert organic solvent, the invention pertains to the stabilized vanadium tetrachloride solution obtains therefrom.

It will be further understood that the present invention is especially useful in stabilizing vanadium tetrachloride that will subsequently be employed in polymerization processes while avoiding the problems associated with the stabilizers disclosed in prior art patents, as discussed above.

DETAILED DESCRIPTION OF THE INVENTION

As described above, the essence of the present invention is the discovery that vanadium tetrachloride can be effectively stabilized against decomposition by the use of acyl halides including aromatic monoacyl halides such as benzoyl chloride. The additive is employed in amounts less than about 20 mol % per mol of vanadium metal in the solution. Preferred amounts of the aromatic acyl monohalide range from about 1 to 10 mol %, while the especially preferred amounts are from about 3 to 5 mol %. It will be understood, however, that the amount of aromatic monoacyl halide, incorporated in the vanadium tetrachloride need only be sufficient, under the existing conditions, to prevent substantial decomposition from occurring.

The acyl halide can generally be of the formula

in which R is a bond or a $C_1$–$C_6$ alkyl, alkylene, aryl or arylene group n is 0 or 1, and each individual X is halogen, preferably chlorine. Although benzoyl chloride has been designated as the preferred aromatic monoacyl halide employed in the practice of the invention, it will be understood that other useful stabilizers include alkyl acyl halides such as acetyl chloride, difunctional acyl halides such as, for instance, oxalyl chloride, multifunctional aromatic halides exemplified by phthaloyl chloride, and the like.

In accordance with an important aspect of the present invention, the vanadium tetrachloride to be stabilized is diluted with an inert organic solvent. Hydrocarbon solvents are preferred, with the use of hexane, as well known solvent in the polymerization arts, is especially preferred. Other useful inert organic hydrocarbon or halocarbon solvents include heptane, kerosene, cyclohexane, benzene, octane, nonane, toluene, dichloroethylene, and other solvents known in the art. Neither the particular solvent employed nor the amount of vanadium tetrachloride in solution are critical features of this invention. In general, however, when solvents are employed the concentration of vanadium tetrachloride may vary from 0.001 to 1.0 mol per liter of solution.

As previously mentioned, the stabilized vanadium tetrachloride of the present invention can be effectively employed as catalyst component in processes for polymerizing and co-polymerizing olefins such as ethylene, propylene, and the like. Such polymerization processes are described in the following U.S. Pat. Nos.: 3,622,548, 4,159,965, 4,420,595, 4,435,552, 4,507,449, 4,514,514. In general, such a polymerization process would involve using vanadium tetrachloride as catalyst and an organoaluminum compound as the co-catalyst. The vanadium tetrachloride is dissolved in a solvent, e.g. hexane, in a catalyst make-up zone and then introduced in solution into a polymerization zone from contact with solvent, olefin(s) and the co-catalyst. Following the polymerization reaction, the reaction product mixture is withdrawn from the polymerization zone, quenched, deashed and subjected to a solvent separation step. The separated solvent is recycled to the polymerization zone and to the catalyst make-up zone. Utilizing the present invention, the aromatic acyl monohalide stabilizes the vanadium tetrachloride outside of the polymerization zone.

Although the stabilization of vanadium tetrachloride that is used in polymerization processes is an important aspect of this invention, it should be appreciated that the availability of effectively stabilized vanadium tetrachloride is also important from processes involving the preparation of vanadium trichloride, vanadium dichloride, and organo-vanadium compounds.

Referring again to the polymerization U.S. patents listed above, it will be noted that in U.S. Pat. No. 4,558,025 that in the formulation of polymerization catalysts acyl halides, including benzoyl chloride, are disclosed as catalyst components. Attention is also directed to U.S. Pat. No. 4,159,965. In these patents the use of acyl halides in formulating catalyst appears based on the former's ability to function as a catalyst activator. In neither of these patents is there any disclosure which teaches or suggests that acyl halides can be effectively used to stabilize vanadium tetrachloride or to have any beneficial activity whatsoever in the absence of the total formulation or, for that matter, outside of the polymerization zone. In column 1 of U.S. Pat. No. 4,420,595 there is a disclosure pertaining to the teachings of Dutch Patent applications Nos. 6410447 and 6712044 of utilizing various halogenated compounds as polymerization catalyst promoters or activators. Named activators include alpha-trichlorotoluene and perchlorocrotonic acid compounds. This disadvantage of using compounds with a high chlorine content is recognized.

In copending U.S. Patent Application Ser. No. 050,946 the invention is concerned with the stabilization of vanadium tetrachloride, outside the polymerization zone, utilizing halogenated organic compounds having at least two halogen atoms attached to the same carbon atom. The vanadium tetrachloride may be dissolved in an inert organic compound such as hexane; while the preferred additive is alkyl perchlorocrotonates with butyl perchlorocrontonate (BPCC) being especially preferred.

As the data set forth below will demonstrate, the use of the aromatic monoacyl halides not only has the advantage of having a low halogen content but surprisingly is markedly superior to the use of trichlorobenzene or butyl perchlorocrontonate for the stabilization of vanadium tetrachloride. Another advantage of aromatic acyl halides such as benzoyl chloride is their ability to undergo substantially complete hydrolysis during deashing of the resulting polymer thereby forming water soluble hydrolysis products which can be readily removed from the polymer by conventional aqueous deashing techniques. This produces a product substantially free of undesirable halogenated by-product contamination which is present when BPCC and the like is used. The reasonf for such results are not fully understood at this time.

The invention will be more fully understood by reference to the following illustrative embodiments.

EXAMPLE 1

A series of comparative runs utilizing various additives to determine the latter's affect on vanadium tetrachloride stabilization. The results are tabulated below.

To start with, a stock solution of 100 g of $VCl_4$ in 1500 ml of hexane was made in a volumetric flask and kept at 0° C. This solution was used for not more than 48 hours. Actual decomposition experiments were run in 1000 ml flask connected to the nitrogen manifold and filled with 1000 ml of hexane containing 10.0 g of $VCl_4$ (1% $VCl_4$). This solution was made by appropriately diluting the stock $VCl_4$ solution with purified polymerization grade hexane (<1 ppm $O_2$, <1 ppm water). The additives were added at this stage. The flask was stirred magnetically and maintained at the reaction temperature by heating or cooling. The accuracy of temperature over the reaction time is estimated to be ±1° C. The reaction flask was also kept dark and away from light source since $VCl_4$ is photosensitive.

$VCl_4$ decomposition was monitored by UV-VIS spectroscopy with a Perkin Elmer Lambda 7 graphics spectrometer operating in the visible range 600–300 nm.

$VCl_4$ has an absorption maxima at 410 nm which was used to monitor the concentration of $VCl_4$. Shorter wavelengths were not used becausete of interference in these regions from precipitates formed during the decomposition reactions. Absorption were determined using this solution in a variable path length cell capable of path lengths of 0.1–0.2 mm, which is the region of most accurate data for this $VCl_4$ concentration. All $VCl_4$ solutions, before and during spectral measurements, were protected from atmospheric moisture and oxygen using sealed septa and Schlenck line technique for transfer and manipulation of solution. Hexane was used as the standard in all measurements and all data are corrected for interal absorbances using standard Perkin Elmer data handling packages.

All the data is normalized with respect to the original $VCl_4$ absorbance; this removes the variation in the data due to dilution discrepancies. For purposes of reference the mean value of the absorbance at 410 nm is 1.6±0.05 A for the $VCl_4$ solution used in these experiments.

The comparative decomposition data of $VCl_4$ (1% solution in hexane) at 65° C. showing the percentage of $VCl_4$ maintained in the presence of these additions follows:

TABLE I

| Time, Hours | % of $VCl_4$ Retained | | | | | 0% Mole BPCC/TCT/BZC |
|---|---|---|---|---|---|---|
| | 10% Mole | | | 3% Mole | | |
| | BPCC | TCT | BZC | BZC | BPCC | |
| 1 | 99 | 99 | 99 | 99 | 99 | 97 |
| 2 | 99 | 99 | 99 | 99 | 99 | 95 |
| 3 | 99 | 99 | 100 | 99 | 99 | 92 |
| 4 | 99 | 99 | 99 | 99 | 98 | 87 |
| 5 | 99 | 98 | 99 | 100 | — | — |
| 6 | 98 | — | — | — | 91 | 78 |
| 7.5 | 98 | 94 | 99 | 98 | — | — |
| 8 | 96 | — | 99 | 96 | 87 | 60 |
| 9.5 | 94 | — | 99 | 90 | — | — |
| 11 | — | — | 98 | — | — | — |
| 12.5 | — | — | 98 | — | — | — |
| 14 | — | — | 96 | — | — | — |

BPCC = Butyl Perchlorocontonate
TCT = Trichlorotoluene
BZC = Benzoyl Chloride

The above data demonstrate the marked superiority of benzoyl chloride in stabilizing solutions of VCl$_4$ against decomposition, e.g., to VCl$_3$.

Further advantages of the use of benzoyl chloride include the relative inexpensiveness of benzoyl chloride compared to other proposed stabilization additives; and when the stabilized vanadium tetrachloride solution is used in formulating polymerization processes, the benzoyl chloride has no discernible effect on the polymerization characteristics of vanadium tetrachloride as well as being easily converted to non-halogenated, innocuous compounds by reaction with the aluminum alkyl cocatalyst to form ethyl phenyl ketone and by reaction with moisture to form benzoic acid.

EXAMPLE 2

This example demonstrates use of VCl$_4$ catalyst stabilized with benzoyl chloride in amounts up to 15 mole % on VCl$_4$, and illustrates the absence of deleterious effect on catalyst performance. The conditions of the polymerization are shown in Table II and the polymer properties in Table III.

TABLE II

| Reactor | 3.875 liter CFSTR |
|---|---|
| Temperature | 40° C. |
| Pressure | 413 kPa |
| Residence time | 10 min. |
| Feeds to Reactor | |
| Hexane | 40.8 kg/hr |
| Ethylene | 1159 g/hr |
| Propylene | 1632 g/hr |
| 5-Ethylidene-w-Norbornene | 19.3 g/hr |
| Hydrogen | 50 wppm on Ethylene |
| VCl$_4$ | 7.52 g/hr |
| Ethyl Aluminum Sesqin Chloride for 5.5 Al/V (Molar Ratio) | |
| Benzoyl Chloride (premixed with VCl$_4$) - as in Table III | |

TABLE III

| | BZC[1] | Polymer Analysis[3] | | |
|---|---|---|---|---|
| Polymer | mole % on VCl$_4$ | Polymerization Ratio (g/hr)[2] | C$_2$ wt. % | N$_2$ (1 + 8) 127° C. |
| A | 0 | 2472 | 41.2 | 16.0 |
| B | 3 | 2423 | 41.8 | 17.5 |
| C | 6 | 2462 | 41.2 | 19.0 |
| D | 10 | 2468 | 42.1 | 18.2 |
| E | 15 | 2486 | 41.0 | 18.8 |

[1]Added benzoyl chloride, present in VCl$_4$ liquid.
[2]Grams per hour of polymer.
[3]Analysis performed on dried, deashed polymer. Deashing accomplished by added aqueous HCl (25 × excess) to polymerization reactor effluent; water washed; and dried on a hot rubber mill at 150° C.

Although the present invention is illustrative in connection with the above examples, it will be understood that the invention is subject to modifications and variations without departing from its broad concept.

What is claimed is:

1. A method of stabilizing vanadium tetrachloride against decomposition into vanadium trichloride which comprises incorporating therein an amount of an acyl halide effective to preclude said decomposition, wherein said acyl halide is of the formula $$\underset{(XC)_nRCX}{\overset{O\quad O}{\underset{\|}{\|}}}$$

in which R is a bond or a C$_{1-6}$ alkyl, alkylene, aryl or arylene group, n is 0 or 1 and X is halogen, and wherein the amount of said acyl halide ranges from about 0.1 to 10 mol % of vanadium.

2. The method of claim 1 wherein the vanadium tetrachloride is in solution with an inert organic solvent.

3. The method of claim 2 wherein said inert organic solvent is a hydrocarbon or halocarbon.

4. The method of claim 1 wherein n is 0, R is C$_{1-6}$ alkyl or phenyl and X is chloro.

5. The method of claim 1 wherein the acyl halide is benzoyl chloride.

6. The method of claim 1 wherein the amount of said acyl halide ranges from about 3 to 5 mol %.

7. A method of stabilizing vanadium tetrachloride against decomposition into vanadium trichloride which comprises incorporation therein an amount of an acyl halide effective to preclude said decomposition wherein the acyl halide is of the formula $$\underset{(XC)_nRCX}{\overset{O\quad O}{\underset{\|}{\|}}}$$

in which n is 1, R is a bond, C$_{1-6}$ alkylene or phenylene and X is chloro.

8. A stabilized vanadium tetrachloride composition comprising vanadium tetrachloride, an inert organic solvent, and an amount of an acyl halide effective to preclude substantial decomposition of said vanadium tetrachloride, wherein said acyl halide is of the formula $$\underset{(XC)_nRCX}{\overset{O\quad O}{\underset{\|}{\|}}}$$

in which R is a bond or a C$_{1-6}$ alkyl, alkylene, aryl or arylene group, n is 0 or 1 and X is halogen, and wherein the amount of said acyl halide ranges from about 0.1 to 10 mol % per mol of vanadium.

9. The stabilized vanadium tetrachloride composition of claim 8 wherein said inert organic solvent is a hydrocarbon or halocarbon.

10. The stabilized vanadium tetrachloride composition of claim 8 wherein the amount of the acyl halide ranges from about 3 to 5 mol %.

11. The stabilized vanadium tetrachloride composition of claim 8 wherein n is 0, R is C$_{1-6}$ alkyl or phenyl and X is chloro.

12. The stabilized vanadium tetrachloride composition of claim 8 wherein the acyl halide is benzoyl chloride.

13. The stabilized vanadium tetrachloride composition of claim 12 wherein the solvent is a hydrocarbon.

14. A stabilized vanadium chloride composition comprising vanadium tetrachloride, an inert organic solvent, and an amount of an acyl halide effective to preclude substantial decomposition of said vanadium tetrachloride wherein the acyl halide is of the formula $$\underset{(XC)_nRCX}{\overset{O\quad O}{\underset{\|}{\|}}}$$

in which n is 1, R is a bond, C$_{1-6}$ alkylene or phenylene and X is chloro.

* * * * *